(12) United States Patent
Song et al.

(10) Patent No.: US 7,259,225 B2
(45) Date of Patent: Aug. 21, 2007

(54) THERMOSENSITIVE POLY (ORGANOPHOSPHAZENES), PREPARATION METHOD THEREOF AND INJECTABLE THERMOSENSITIVE POLYPHOSPHAZENE HYDROGELS USING THE SAME

(75) Inventors: Soo-Chang Song, Seoul (KR); Bae-Houn Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 137 days.

(21) Appl. No.: 10/835,378

(22) Filed: Apr. 28, 2004

(65) Prior Publication Data

US 2005/0020808 A1 Jan. 27, 2005

(30) Foreign Application Priority Data

Jul. 25, 2003 (KR) ............... 10-2003-0051521

(51) Int. Cl.
*C08G 63/02* (2006.01)

(52) U.S. Cl. .............. 528/272; 524/725; 524/726; 524/755; 524/765; 524/770; 525/54.1; 525/538; 525/540; 528/332; 528/399; 528/400; 528/422

(58) Field of Classification Search ........... 528/332, 528/399, 400, 422; 525/54.1, 538, 540; 524/725, 524/726, 755, 765, 770
See application file for complete search history.

(56) References Cited

U.S. PATENT DOCUMENTS 6,319,984 B1 11/2001 Song et al.
2002/0014616 A1* 2/2002 Allcock et al. ............ 252/500

FOREIGN PATENT DOCUMENTS

KR 1020000002785 A1 1/2000
KR 1020010047025 A1 6/2001

OTHER PUBLICATIONS

Jeong, Byeongmoon, et al., "Thermosensitive sol-gel reversible hydrogels", Advanced Drug Delivery Reviews, 2002, vol. 54, pp. 37-51.

Hatefi, A., et al., "Biodegradable injectable in situ forming drug delivery systems", Journal of Controlled Release, 2002, vol. 80, pp. 9-28.

Jeong, B., et al., "New biodegradable polymers for injectable drug delivery systems", Journal of Controlled Release, 1999, vol. 62, pp. 109-114.

Song, Soo-Chang, et al., "A New Class of Biodegradable Thermosensitive Polymers. I. Synthesis and Characterization of Poly(organophosphazenes) with Methoxy-Poly (ethylene glycol) and Amino Acid Esters as Side Groups", Macromolecules, 1999, vol. 32, pp. 2188-2193.

Lee, Sang Beom, et al., "A New Class of Biodegradable Thermosensitive Polymers. 2. Hydrolytic Properties and Salt Effect on the Lower Critical Solution Temperature of Poly(organophosphazenes) with Methoxylpoly(ethylene glycol) and Amino Acid Esters as Side Groups", Macromolecules, 1999, vol. 32, pp. 7820-7827.

Lee, Bae Hoon, et al., "A Thermosensitive Poly(organophosphazene) Gel", Macromolecules, 2002, vol. 35, pp. 3876-3879.

* cited by examiner

*Primary Examiner*—Terressa Boykin
(74) *Attorney, Agent, or Firm*—Darby & Darby (57) ABSTRACT

Disclosed are polyphosphazenes of Formula 1 showing a sol-gel behavior with a temperature change, a preparation method thereof, and injectable thermosensitive polyphosphazene hydrogels using the same

[Formula 1]

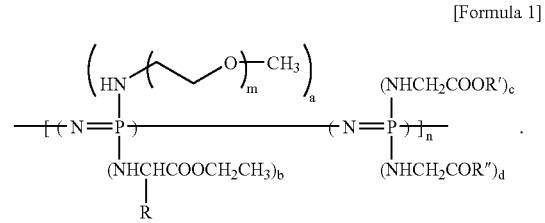

10 Claims, 4 Drawing Sheets

FIG. 1

Sol (<30°C)  →←Temp→  Gel (37°C)

THERMOSENSITIVE POLY (ORGANOPHOSPHAZENES), PREPARATION METHOD THEREOF AND INJECTABLE THERMOSENSITIVE POLYPHOSPHAZENE HYDROGELS USING THE SAME

BACKGROUND OF THE INVENTION

1. Field of the Invention

The present invention relates to a biodegradable polyphosphazene polymer showing a sol-gel behavior by a temperature change in aqueous solution, a preparation method thereof, and injectable thermosensitive polyphosphazene hydrogels using the same.

2. Description of the Related Art

Generally, a hydrogel refers to a three-dimensional network structure formed from a polymer existing in aqueous solution. The hydrogel is formed by a chemical crosslink by a covalent bond or by a physical crosslink through a physical crosslink between molecules.

A network structure formed by the physical crosslink is different from that formed by the chemical crosslink in that the structure is formed not by a crosslinking points like in the covalent bond but by a physical junction zone. A polymer shows a sensitivity against an external stimulus such as temperature, pH, electricity, and etc., and a polymer showing a drastic phase transition by a temperature change is called as a thermosensitive polymer. The thermosensitive polymer shows a phase transition behavior according to a temperature change in aqueous solution, and the phase transition is reversibly performed from sol to gel and from gel to sol according to a temperature change. Especially, in case of a neutral polymer, it is regarded that a physical network structure is formed by a hydrophobic interaction, and the hydrophobic interaction is observed in aqueous solution of a polymer having a side chain such as an aliphatic chain, a fluorine chain, an aromatic chain, etc.

A hydrogel formed by the physical crosslink does not use a chemical crosslinking agent harmful to a body, thereby being spotlighted as a drug delivering material. A polymer showing a sol-gel characteristic by a temperature change includes a poly (N-isopropyl acrylamide), polyethyleneoxide-polypropyleneoxide-polyethyleneoxide (PEO-PPO-PEO) and polyethyleneoxide-polylactic, glycolic acid-polyethyleneoxide (PEO-PLGA-PEO), and etc., and researches for using them as injectable drug delivering material are actively being underway (*Advanced Drug Delivery Reviews*, 54, 37 (2002), *Journal of Controlled Release*, 80, 9 (2002)).

However, poly (N-isopropyl acrylamide) is disadvantageous in that it is cytotoxic and not dissolvable in vivo. Also, F127 of the PEO-PPO-PEO (Poloxamer® or Fluronic®) shows a sol-gel behavior by a temperature change in a concentration of not less than about 20% of weight, but when used for a long period, F127 not only increases the concentration of cholesterol in plasma and triglycerides but also is not dissolved in vivo.

PEO-PLGA-PEO(Regel®) is dissolved in a physiological condition and becomes a gel state at a temperature near a body temperature, thereby being researched as an agent for locally delivering an anti-cancer drug. However, that polymer was reported to show a sol-gel characteristic only in a high concentration of more than about 16 weight % (*Journal of Controlled Release*, 62, 109 (1999)).

The present inventors have reported that polyphosphazene polymers obtained by substituting polydichlorophosphazene with methoxypolyethyleneglycol and amino acid ester are dissolved in water under a predetermined temperature, but have a phase transition behavior in a temperature more than the certain temperature when a temperature is gradually increased and are gradually hydrolyzed in aqueous solution (*Macromolecules* 32, 2188 (1999), *Macromolecules* 32, 7820 (1999), *Macromolecules* 35, 3876 (2002), Korean patent No. 259,367, No. 315,630 and U.S. Pat. No. 6,319, 984 and etc.).

However, the phase transition behavior of the polyphosphazene polymers disclosed in said theses or patents is mainly a sol-precipitation. Also, in case of polymer showing a sol-gel behavior, a gel intensity is weak in a physiological condition or a phenomenon of a gel contraction is generated, thereby having a limitation in being applied as a drug delivering material.

SUMMARY OF THE INVENTION

Therefore, an object of the present invention is to provide a polyphosphazene polymer suitable for being used as a material of an injectable drug delivering system and having a biodegradable sol-gel behavior by a temperature change, and an excellent gel characteristic at a temperature near a body temperature, a preparation method thereof, and injectable thermosensitive biodegradable hydrogels using the same.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, and examples of which are illustrated in the accompanying drawings.

The present invention relates to a polyphosphazene polymer represented by Formula 1, a preparation method thereof, and injectable thermosensitive polyphosphazene hydrogels using the same.

[Formula 1]

wherein,

R represents $CH_2CH(CH_3)_2$, $CH(CH_3)C_2H_5$, or $C_7H_7$, R' denotes $CH_2COOC_2H_5$ or $CH(CH_3)COOC_2H_5$, and R" denotes $OC_2H_5$, $NHCH_2COOC_2H_5$, $NHCH_2COOC_7H_7$, $NHCH(CH_2CH(CH_3)_2)COOC_2H_5$ or $NHCH(CH(CH_3)C_2H_5)COOC_2H_5$;

a, b, c and d denote contents of each substituent, wherein each of a and b is 0.1-1.9 and each of c and d represents 0-1.9, respectively, and a+b+c+d=2.0;

n denotes a degree of polymerization of a polyphosphazene and has a value of 10-10000; and m denotes the number of a repeating unit of aminomethoxypolyethyleneglycol substituent and has a value of 10-50.

The present invention solved a problem that a polyphosphazene polymer of *Macromolecules* 32, 2188 (1999), *Macromolecules* 32, 7820 (1999), *Macromolecules* 35, 3876 (2002), Korean patent No. 259,367, No. 315,630 and U.S. Pat. No. 6,319,984, having a phase transition do not have a sol-gel characteristic suitable for being used as a drug delivering material. The present inventors discovered that a gelation temperature and a gel viscosity of a polyphosphazene polymer greatly vary according to a kind of amino acid ester, molecular weight of aminomethoxypolyethyleneglycol, and respective contents of them and the gel characteristic of a polyphosphazene polymer can be controlled by using said characteristic, and thereby completed the present invention.

Accordingly, the polyphosphazene polymer of the present invention has as a substituent, a polyethyleneglycol which has a greater molecular weight than that substituted at the polyphosphagene polymers disclosed in said documents, and a ratio of a hydrophilic substituent and a hydrophobic substituent existing in the polyphosphazene polymer was controlled to have an excellent gel characteristic even at a temperature near a body temperature, thereby having a physical characteristic suitable for being used as an injectable drug delivering material.

In the present invention, the hydrophilic substituent is aminomethoxypolyethyleneglycol having a molecular weight of at least 550, preferably 550-2500, and the hydrophobic substituent is amino acid ester selected from the group consisting of leucineethylester, isoleucineethylester, phenylalanineethylester, glycinethylester, glycylglycinbenzylester, glycylglycinethylester, glycylleucineethylester and glycylisoleucineethylester. In the meantime, depsipeptide ester selected from the group consisting of ethyl-2-(O-glycyl)glycolate and ethyl-2-(O-glycyl)lactate is a substituent for controlling a decomposition rate.

Next, a preparation method of the polyphosphazene polymer represented as the Formula I will be explained.

In the present invention, a polydichlorophosphazene linear polymer having an average molecular weight of $10^3$-$10^5$ of the following Formula 3 was obtained by a thermal polymerization of phosphazene trimer of the following Formula 2 as described in *Macromolecules*, 28, 7566 (1995) besides Y. S. Sohn, and it was used as a starting material.

[Formula 2]

[Formula 3]

A preparation method of the polyphosphazene polymer of Formula 1 according to the present invention comprises the steps of:

(1) reacting a compound of Formula 3 with amino acid ethylester of Formula 4 or a salt thereof;

$H_2NCH(R)COOCH_2CH_3$ [Formula 4]

(2) reacting the product of the step (1) with depsipeptide ester represented of Formula 5 or a salt thereof, or with amino acid ester of Formula 6 or a salt thereof; and $H_2NCH_2COOR'$ [Formula 5]

$H_2NCH_2COR''$ [Formula 6]

(3) reacting the product of the step (2) with aminomethoxypolyethyleneglycol of Formula 7 or a salt thereof to obtain a polyphosphazene polymer of Formula 1.

[Formula 7]

In case of undergoing all the reactions of the steps (1) to (3), a polyphosphazene polymer of Formula 1 wherein c or d is not 0 is obtained, and in case that the product of the step (1) is used as a starting material for a reaction of step (3) without undergoing the step (2), a polyphosphazene polymer of Formula 1 wherein each of c and d is respectively 0 is obtained.

The following Reaction Scheme 1 shows a summarized preparation processes of the polyphosphazene polymer according to the present invention.

[Reactions Scheme 1]

In said Formulas 3 to 7 and the Reaction Scheme 1, R, R', R", a, b, c, d, n and m are the same as defined in Formula 1.

Hereinafter, a preparation method of the polyphosphazene polymer according to the present invention as shown in the Reaction Scheme 1 will be explained in more detail.

In the step (1), the compound of the Formula 3 is reacted with 0.1-1.9 equivalents of amino acid ethylester based on said one equivalent of compound of the formula 3 and represented as a Formula 4 or a salt thereof in the presence of 4 equivalents of triethylamine. The salt of amino acid ethylester represented as the Formula 4 is preferably hydrogen chloride salt. A reaction solvent includes tetrahydrofuran(THF), dioxane, dimethylformamide(DMF), chloroform, or toluene, and the reaction is performed for about 12-72 hours in a temperature of −60-50° C.

In the step (2), a product of the step (1) is reacted with 0-1.9 equivalents of depsipeptide ester of Formula 5 or a salt thereof, or with amino acid ester, dipeptide ester of Formula 6 or a salt thereof, in the presence of 0-4 equivalents of triethylamine. The salt of the compound of Formula 5 or Formula 6 is preferably oxalate or hydrogen chloride salt. As a non-limiting example of a reaction solvent, acetonitrile can be used. A reaction temperature is preferably 0-45° C., and a reaction time is about 12-72 hours.

The aminomethoxypolyetheleheglycol of Formula 7 used as a reaction material in the step (3) is prepared by the following method.

First, one equivalent of dried methoxypolyethyleneglycol is reacted with one equivalent of 4-toluenesulfonyl chloride in the presence of two equivalents of triethylamine for 12 hours by using chloroform as a solvent. Then, two equivalents of sodium azide is added to the mixture and reacted for 12-24 hours at a temperature of 70-80° C. in dimethylformami or acetnytril as a solvent, thereby obtaining methoxypolyethyleneglycolazide. Subsequently, methoxypolyethyleneglycolazide is converted into aminomethoxypolyethyleneglycol by using two equivalents of triphenylphosphine and ten equivalents of water. Then, to 200 g of aminomethoxypolyethyleneglycol as obtained, 200 ml of benzene is added and distilled at a temperature of 70-80° C. so as to remove excess water. Then, the mixture is put to oil bath of 80-90° C., and dried for three days in a vacuum state. Then, molecular sieves of 3 Å is put in a sufficient amount, then filled with dried nitrogen and a necessary amount is taken by a syringe, thereby being used in the reaction of the step (3).

In the step (3), a product of the step (2) is reacted with two equivalents of aminomethoxypolyethyleneglycol of Formula 6 based on the remaining chlorines in the presence of four equivalents of triethylamine, thereby substituting all of the chlorines remained in the product of the step (2) with aminomethoxyglycol. At this time, as a reaction solvent, tetrahydrofuran, dioxane, chloroform or toluene are preferably used, but these are non-limiting examples only. A reaction temperature is 40-50° C., and a reaction time is about 48-72 hours.

In the steps (1) to (3), a product of each step can be used in the next step without purification, and a pure desired product can be recovered from a reaction mixture of the step (3) by the following method.

First, the reaction mixture is centrifuged or filtered to remove the precipitates (for example, triethylammonium chloride, triethylammonium salt of oxalic acid, etc.) from the reaction mixture and the filtrate is concentrated under a reduced pressure until a small quantity of solvent remains. Then, the concentrated liquid is dissolved in THF, and excess amount of hexane is added to induce precipitation of a product and then filtered, which are repeated 2 to 3 times, thereby removing un-reacted aminomethoxypolyethyleneglycol, amino acid ester and depsipeptide. A solid obtained by said processes is dissolved in a small amount of methanol, sequentially dialyzed by methanol and distilled water, and dried in a low temperature to obtain a pure compound of Formula 1.

The present invention also relates to thermosensitive hydrogels for injectable drug delivering material containing a polyphosphazene polymer of Formula 1 and having a distinct sol-gel characteristic with a temperature change. In the present invention, the said hydrogels are the polyphosphazene polymer of Formula 1 dissolved in buffering solution, acid solution, base solution, salt solution or water in a concentration of 2-30 weight %, preferably in a concentration of 7-15 weight %.

EXAMPLES

Hereinafter, the present invention will be explained in more detail with reference to preferred embodiments. However, the present invention are not limited to the preferred embodiments. In the following examples, an element analysis of carbon, hydrogen, and nitrogen for a product was performed by Perkin-Elmer C, H, N analyzer of the Characteristic Analysis Lab. of Korea Institute of Science and Technology. In the meantime, hydrogen and phosphorus NMR spectrum was measured by Varian Gemini-300, a glass transition temperature ($T_g$) was measured by Du Pont 1090 differential thermal heat analyzer, and an average molecular weight (Mw) was measured by Waters 1515 pump and a gel transmission chromatography of 2410 differential refractormeter.

A viscosity of the polymer was measured by dissolving the polymer in an aqueous solution of PBS of pH 7.4 in a concentration of 10 weight %, putting the polymer in a chamber of a viscometer (Brookfield DV-III+ Rheometer) provided with an automatic temperature control bath (TC-501), and increasing the temperature in the rate of 0.04° C. per a minute with a shear rate of 0.1-1.7.

Example 1

Preparation of Poly[poly(aminomethoxyethyleneglycol550)(isoleucineethylester)(ethyl-2-(O-glycyl)lactate)], [NP(AMPEG550)$_{0.78}$(IleOEt)$_{1.18}$(GlyLacOEt)$_{0.04}$]

Poly(dichlorophosphazene) (2.00 g, 17.26 mmol) was dissolved in tetrahydrofuran and then put into a dry ice-aceton bath. Then, triethylamine (8.38 g, 82.84 mmol) and isoleucineethylester hydrogen chloride salt (4.05 g, 20.71 mmol) were sequentially added thereto and reacted for 48 hours at room temperature.

To the above reaction solution, a solution of ethyl-2-(O-glycyl)lactate ammonium oxalate (0.152 g, 0.69 mmol) and triethylamine (0.35 g, 3.45 mmol) in acetonitrile (50 ml) was added, and then reacted for 19 hours in ice bath.

Then, poly(aminomethoxyethyleneglycol) (14.24 g, 25.89 mmol) having molecular weight of 550 and triethylamine (5.24 g, 51.78 mmol) were added thereto, and reacted for 48 hours at 50° C.

The reaction solution was centrifuged or filtered to remove an excess amount of precipitates (Et$_3$N.HCl), and the filtrate was concentrated under a reduced pressure until a small quantity of solvent remained. Then, the concentrated solution was dissolved in THF, and a precipitation of a product was induced by adding excessive hexane and filtered, which were repeated 2 to 3 times. Then, the solid obtained by said processes was dissolved in a small amount of methanol, sequentially dialyzed by methanol and distilled water for 5 days each, and then dried in a low temperature, thereby obtaining 6.7 g (58% yield) of a final product of [NP(AMPEG550)$_{0.78}$(IleOEt)$_{1.18}$(GlyLacOEt)$_{0.04}$].

Composition formula: C$_{38}$H$_{76}$N$_4$O$_{17}$P Elemental analysis: C,49.52; H, 8.89; N, 6.79 Theoretical value: C, 49.80; H, 8.64; N, 6.45 Hydrogen NMR spectrum (CDCl$_3$, ppm): δ 0.8-1.0 (b, 6H, —NHCH(CH$_2$CH(C$\underline{H}_2$)$_2$COOCH$_2$CH$_3$), δ 1.1-1.3 (b, 3H, —NHCH(CH$_2$CH(CH$_3$)$_2$COOCH$_2$C$\underline{H}_3$, —NHCH$_2$COOCH(CH$_3$)COOCH$_2$C$\underline{H}_3$), δ 1.4-1.6 (b, 2H, —NHCH(C$\underline{H}_2$CH(CH$_3$)$_2$COOCH$_2$CH$_3$, —NHCH$_2$COOCH(C$\underline{H}_3$)COOCH$_2$CH$_3$), δ 1.6-1.9 (b, 1H, —NHCH(CH$_2$C$\underline{H}$(CH$_3$)$_2$COOCH$_2$CH$_3$), δ 2.9-3.2 (b, 2H, —NHC$\underline{H}_2$CH$_2$O(CH$_2$CH$_2$O)$_{10}$CH$_3$), δ 3.4 (s, 3H, —NHCH$_2$CH$_2$O(CH$_2$CH$_2$O)$_{16}$C$\underline{H}_3$), δ 3.5-3.9 (b, 95H, —NHCH$_2$C$\underline{H}_2$O(C$\underline{H}_2$C$\underline{H}_2$O)$_{10}$CH$_3$, —NHC$\underline{H}_2$COOCH(CH$_3$)COOCH$_2$CH$_3$, —NHC$\underline{H}$(CH$_2$CH(CH$_3$)$_2$COOCH$_2$CH$_3$), δ 4.04-4.4 (b, 4H, —NHCH(CH$_2$CH(CH$_3$)$_2$COOC$\underline{H}_2$CH$_3$, —NHCH$_2$COOCH(CH$_3$)COOC$\underline{H}_2$CH$_3$), δ 5.0-5.1 (b, 1H, —NHCH$_2$COOC$\underline{H}$(CH$_3$)COOCH$_2$CH$_3$) Phosphorous NMR spectrum (CDCl$_3$, ppm): δ 17.9 Average molecular weight (M$_w$): 27000 Maximum viscosity (V$_{max}$): 312.8 Pa·s Maximum gel temperature (T$_{max}$): 43° C.

Example 2

Preparation of Poly[poly(aminomethoxyethyleneglycol550)(isoleucineethylester)(glycylglycinethylester)phosphazene], [NP(AMPEG550)$_{0.70}$(IleOEt)$_{1.20}$(GlyGlyOEt)$_{0.10}$]

By the same method as that of Example 1, poly(dichlorophosphazene) (2.00 g, 17.26 mmol), triethylamine (4.19 g, 41.42 mmol) and isoleucineethylester hydrogen chloride salt (4.05 g, 20.71 mmol) in the first step, glycylglycinethylester hydrogen chloride salt (0.34 g, 1.73 mmol) and triethylamine (0.70 g, 6.92 mmol) in the second step, and poly(aminomethoxyethyleneglycol) (13.29 g, 24.16 mmol) of a molecular weight of 550 and triethylamine (4.89 g, 48.32 mmol) in the third step were respectively used for reaction, thereby obtaining 8.2 g (70% yield) of a final product, [NP(AMPEG550)$_{0.70}$(IleOEt)$_{1.20}$(GlyGlyOEt)$_{0.10}$].

Composition formula: C$_{37}$H$_{75}$N$_4$O$_{16}$P Elemental analysis: C, 50.01; H, 8.59; N, 6.90 Theoretical value: C, 49.80; H, 8.56; N, 6.84 Hydrogen NMR spectrum (CDCl$_3$, ppm): δ 0.8-1.0 (b, 6H, —NHCH(CH$_2$CH(C$\underline{H}_3$)$_2$COOCH$_2$CH$_3$), δ 1.1-1.3 (b, 6H, —NHCH(CH$_2$CH(CH$_3$)$_2$COOCH$_2$C$\underline{H}_3$, —NHCH$_2$CONHCH$_2$COOCH$_2$C$\underline{H}_3$), δ 1.4-1.6 (b, 2H, —NHCH(C$\underline{H}_2$CH(CH$_3$)$_2$COOCH$_2$CH$_3$), δ 1.6-1.9 (b, 1H, —NHCH(CH$_2$C$\underline{H}$(CH$_3$)$_2$COOCH$_2$CH$_3$), δ 2.9-3.2 (b, 2H, —NHC$\underline{H}_2$CH$_2$O(CH$_2$CH$_2$O)$_{10}$CH$_3$), δ 3.4 (s, 3H, —NHCH$_2$CH$_2$O(CH$_2$CH$_2$O)$_{10}$C$\underline{H}_3$), δ 3.5-3.9 (b, 95H, —NHCH$_2$C$\underline{H}_2$O(C$\underline{H}_2$C$\underline{H}_2$O)$_{10}$CH$_3$, —NHC$\underline{H}_2$CONHCH$_2$COOCH$_2$CH$_3$, —NHC$\underline{H}$(CH$_2$CH(CH$_3$)$_2$COOCH$_2$CH$_3$) δ 4.0-4.4 (b, 4H, —NHCH(CH$_2$CH(CH$_3$)$_2$COOC$\underline{H}_2$CH$_3$, —NHCH$_2$CONHC$\underline{H}_2$COOCH$_2$CH$_3$, —NHCH$_2$CONHCH$_2$COOCHC$\underline{H}_2$CH$_3$), Phosphorous NMR spectrum (CDCl$_3$, ppm): δ 18.1 Average molecular weight (M$_w$): 41000 Maximum gel viscosity (V$_{max}$): 550.0 Pa·s Maximum gel temperature (T$_{max}$): 39° C.

Example 3

Preparation of Poly[poly(aminomethoxyethyleneglycol550)(isoleucineethylester)phosphazene], [NP(AMPEG550)$_{0.80}$(IleOEt)$_{1.20}$]

Poly(dichlorophosphazene) (2.00 g, 17.26 mmol) was dissolved in THF and then put into a dry ice-aceton bath, then isoleucineethylester hydrogen chloride salt (4.05 g, 20.71 mmol) and triethylamine (8.38 g, 82.84 mmol) were sequentially added thereto and reacted for 48 hours at room temperature. Then, poly(aminomethoxyethyleneglycol) (15.19 g, 27.62 mmol) having a molecular weight of 550 and triethylamine (5.59 g, 55.24 mmol) were added thereto and reacted for 48 hours at 50° C.

The product was recovered from the reaction solution by the same method as described in Example 1, thereby obtaining 7.2 g (62% yield) of a final product, [NP(AMPEG550)$_{0.80}$(IleOEt)$_{1.20}$].

Composition formula: C$_{31}$H$_{64}$N$_3$O$_{13}$P Elemental analysis: C, 50.45; H, 8.90; N, 6.38 Theoretical value: C, 49.95; H, 8.62; N, 6.24 Hydrogen NMR spectrum(CDCl$_3$, ppm): δ 0.8-1.0 (b, 6H, —NHCH(CH$_2$CH(C$\underline{H}_3$)$_2$COOCH$_2$CH$_3$), δ 1.1-1.3 (b, 3H, —NHCH(CH$_2$CH(CH$_3$)$_2$COOCH$_2$C$\underline{H}_3$), δ 1.4-1.6 (b, 2H, —NHCH(C$\underline{H}_2$CH(CH$_3$)$_2$COOCH$_2$CH$_3$), δ 1.6-1.9 (b, 1H, —NHCH(CH$_2$C$\underline{H}$(CH$_3$)$_2$COOCH$_2$CH$_3$), δ 2.9-3.2 (b, 2H, —NHC$\underline{H}_2$CH$_2$O(CH$_2$CH$_2$O)$_{10}$CH$_3$), δ 3.4 (s, 3H, —NHCH$_2$CH$_2$O(CH$_2$CH$_2$O)$_{16}$C$\underline{H}_3$H), δ 3.5-3.9 (b, 95H, —NHCH$_2$C$\underline{H}_2$O(C$\underline{H}_2$C$\underline{H}_2$O)$_{10}$CH$_3$, —NHC$\underline{H}$(CH$_2$CH(CH$_3$)$_2$COOCH$_2$CH$_3$), δ 4.0-4.4 (b, 4H, —NHCH(CH$_2$CH(CH$_3$)$_2$COOC$\underline{H}_2$CH$_3$) Phosphorous NMR spectrum(CDCl$_3$, ppm): δ 19.1 Average molecular weight (M$_w$): 42000 Maximum viscosity (V$_{max}$):400.0 Pa·s Maximum gel temperature (T$_{max}$): 40° C.

Example 4

Preparation of Poly[poly(aminomethoxyethyleneglycol750)(isoleucineethylester)phosphazene], [NP(AMPEG750)$_{0.65}$(IleOEt)$_{1.35}$]

By the same method as described in Example 3, poly(dichlorophosphazene) (2.00 g, 17.26 mmol) and isoleucineethylester hydrogen chloride salt (4.73 g, 24.16 mmol) were reacted in the presence of triethylamine (9.78 g, 96.64 mmol), and then reacted with poly(aminomethoxyethyleneglycol) (15.53 g, 20.71 mmol) having a molecular weight of 750 in the presence of triethylamine (4.19 g, 41.42 mmol), thereby obtaining 9.0 g (70% yield %) of a final product [NP(AMPEG750)$_{0.65}$(IleOEt)$_{1.35}$].

Composition formula: $C_{41}H_{84}N_3O_{18}P$ Elemental analysis: C, 51.32; H, 8.96; N, 5.21 Theoretical value: C, 52.01; H, 8.91; N, 5.64 Hydrogen NMR spectrum(CDCl$_3$, ppm): δ 0.8-1.0 (b, 6H, —NHCH(CH$_2$CH(C$\underline{H}_3$)$_2$COOCH$_2$CH$_3$), δ 1.1-1.3 (b, 3H, —NHCH(CH$_2$CH(CH$_3$)$_2$COOCH$_2$C$\underline{H}_3$), δ 1.4-1.6 (b, 2H, —NHCH(C$\underline{H}_2$CH(CH$_3$)$_2$COOCH$_2$CH$_3$), δ 1.6-1.9 (b, 1H, —NHCH(CH$_2$C$\underline{H}$(CH$_3$)$_2$COOCH$_2$CH$_3$), δ 2.9-3.2 (b, 2H, —NHC$\underline{H}_2$CH$_2$O(CH$_2$CH$_2$O)$_{16}$CH$_3$), δ 3.4 (s, 3H,—NHCH$_2$CH$_2$O(CH$_2$CH$_2$O)$_{16}$C$\underline{H}_3$), δ 3.5-3.9 (b, 95H, —NHCH$_2$C$\underline{H}_2$O(C$\underline{H}_2$C$\underline{H}_2$O)$_{16}$CH$_3$, —NHC$\underline{H}$(CH$_2$CH(CH$_3$)$_2$COOCH$_2$CH$_3$), δ 4.0-4.4 (b, 4H, —NHCH(CH$_2$CH(CH$_3$)$_2$COOC$\underline{H}_2$CH$_3$) Phosphoous NMR spectrum(CDCl$_3$, ppm): δ 17.9 Average molecular weight (M$_w$): 22000 Maximum gel viscosity (V$_{max}$): 680.0 Pa·s Maximum gel temperature (T$_{max}$): 47° C.

Example 5

Preparation of Poly[poly(aminomethoxyethyleneglycol750)(isoleucineethylester)(glycinethylester) phosphazene], [NP(AMPEG750)$_{0.46}$(IleOEt)$_{1.36}$ (GlyOEt)$_{0.18}$]

By the same method as described in Example 1, poly (dichlorophosphazene) (2.00 g, 17.26 mmol), triethylamine (9.78 g, 96.64 mmol) and isoleucineethylester hydrogen chloride salt (4.73 g, 24.16 mmol) in the first step, triethylamine (1.40 g, 13.80 mmol) and glycinethylester hydrogen chloride salt (0.48 g, 3.45 mmol) in the second step, and poly(aminomethoxyethyleneglycol) (12.95 g, 17.26 mmol) having a molecular weight of 750 and triethylamine(3.49 g, 34.52 mmol) in the third step were respectively used and reacted, thereby obtaining 8.2 g (76% yield) of a final product, [NP(AMPEG750)$_{0.46}$(IleOEt)$_{1.36}$(GlyOEt)$_{0.18}$].

Composition formula: $C_{45}H_{92}N_4O_{20}P$ Elemental analysis: C, 52.01; H, 8.91; N, 6.86 Theoretical value: C, 51.66; H, 8.82; N, 6.75 Hydrogen NMR spectrum(CDCl$_3$, ppm): δ 0.8-1.0 (b, 6H, —NHCH(CH$_2$CH(C$\underline{H}_3$)$_2$COOCH$_2$CH$_3$), δ 1.1-1.3 (b, 3H, —NHCH(CH$_2$CH(CH$_3$)$_2$COOCH$_2$C$\underline{H}_3$, —NHCH$_2$COOCH$_2$C$\underline{H}_3$), δ 1.4-1.6 (b, 2H, —NHCH(C$\underline{H}_2$CH(CH$_3$)$_2$COOCH$_2$CH$_3$), δ 1.6-1.9 (b, 1H, —NHCH(CH$_2$C$\underline{H}$(CH$_3$)$_2$COOCH$_2$CH$_3$), δ 2.9-3.2 (b, 2H, —NHC$\underline{H}_2$CH$_2$O(CH$_2$CH$_2$O)$_{16}$CH$_3$), δ 3.4 (s, 3H, —NHCH$_2$CH$_2$O(CH$_2$CH$_2$O)$_{16}$C$\underline{H}_3$), δ 3.5-3.9 (b, 95H, —NHCH$_2$C$\underline{H}_2$O(C$\underline{H}_2$C$\underline{H}_2$O)$_{16}$CH$_3$, —NHC$\underline{H}_2$COOCH$_2$CH$_3$, —NHC$\underline{H}$(CH$_2$CH(CH$_3$)$_2$COOCH$_2$CH$_3$), δ 4.0-4.4 (b, 4H, —NHCH(CH$_2$CH(CH$_3$)$_2$COOC$\underline{H}_2$CH$_3$, —NHCH$_2$COOC$\underline{H}_2$CH$_3$) Phosphorous NMR spectrum (CDCl$_3$, ppm): δ 17.9 Average molecular weight (M$_w$): 24000 Maximum gel viscosity (V$_{max}$): 1021.2 Pa·s Maximum gel temperature (T$_{max}$): 48° C.

Example 6

Preparation of Poly[poly(aminomethoxyethyleneglycol750)(isoleucineethylester)(ethyl-2-(O-glycyl) glycolate)]phosphazene], [NP(AMPEG750)$_{0.64}$ (IleOEt)$_{1.23}$(GlyGlycOEt)$_{0.13}$]

By the same method as described in Example 1, poly (dichlorophosphazene) (2.00 g, 17.26 mmol), triethylamine (9.10 g, 82.84 mmol) and isoleucineethylester hydrogen chloride salt (4.39 g, 22.44 mmol) in the first step, triethylamine (0.35 g, 3.45 mmol) and ethyl-2-(O-glycyl)glycolate ammonium oxalate (0.19 g, 0.86 mmol) in the second step, and poly(aminomethoxyethyleneglycol) (18.12 g, 24.16 mmol) having a molecular weight of 750 and triethylamine (4.89 g, 48.32 mmol) in the third step were respectively used for reaction, thereby obtaining 7.4 g (62% yield) of a final product, [NP(AMPEG750)$_{0.64}$(IleOEt)$_{1.23}$(GlyGlycOEt)$_{0.13}$].

Composition formula: $C_{47}H_{94}N_4O_{22}P$ Elemental analysis: C, 51.00; H, 8.52; N, 6.90 Theoretical value: C, 50.34; H, 8.44; N, 6.77 Hydrogen NMR spectrum(CDCl$_3$, ppm): δ 0.8-1.0 (b, 6H, —NHCH(CH$_2$CH(C$\underline{H}_3$)$_2$COOCH$_2$CH$_3$), δ 1.1-1.3 (b, 3H, —NHCH(CH$_2$CH(CH$_3$)$_2$COOCH$_2$C$\underline{H}_3$, —NHCH$_2$COOCH$_2$COOCH$_2$C$\underline{H}_3$), δ 1.4-1.6 (b, 2H, —NHCH(C$\underline{H}_2$CH(CH$_3$)$_2$COOCH$_2$CH$_3$), δ 1.6-1.9 (b, 1H, —NHCH(CH$_2$C$\underline{H}$(CH$_3$)$_2$COOCH$_2$CH$_3$), δ 2.9-3.2 (b, 2H, —NHC$\underline{H}_2$CH$_2$O(CH$_2$CH$_2$O)$_{15}$CH$_3$), δ 3.4 (s, 3H,— NHCH$_2$CH$_2$O(CH$_2$CH$_2$O)$_{15}$C$\underline{H}_3$), δ 3.5-3.9 (b, 95H, —NHCH$_2$C$\underline{H}_2$O(C$\underline{H}_2$C$\underline{H}_2$O)$_{15}$CH$_3$, —NHC$\underline{H}_2$COOCH$_2$COOCH$_2$CH$_3$, —NHC$\underline{H}$(CH$_2$CH(CH$_3$)$_2$COOCH$_2$CH$_3$), δ 4.0-4.4 (b, 4H, —NHCH(CH$_2$CH(CH$_3$)$_2$COOC$\underline{H}_2$CH$_3$, —NHCH$_2$COOCH$_2$COOC$\underline{H}_2$CH$_3$), δ 4.54-4.7 (b, 2H, —NHCH$_2$COOC$\underline{H}_2$COOCH$_2$CH$_3$), Phosphorous NMR spectrum (CDCl$_3$, ppm): δ 19.1 Average molecular weight (M$_w$): 10000 Maximum gel viscosity (V$_{max}$): 670.0 Pa·s Maximum gel temperature (T$_{max}$): 53° C.

Example 7

Preparation of Poly[poly(aminomethoxyethyleneglycol1100)(isoleucineethylester)phosphazene], [NP (AMPEG1100)$_{0.84}$(IleOEt)$_{1.16}$]

By the same method as described in Example 3, poly (dichlorophosphazene) (2.00 g, 17.26 mmol) and isoleucineethylester hydrogen chloride salt (4.05 g, 20.71 mmol) were reacted in the presence of triethylamine (4.19 g, 41.42 mmol), and then reacted with poly(aminomethoxyethyleneglycol) (30.38 g, 27.62 mmol) of a molecular weight of 1100 in the presence of triethylamine (5.59 g, 55.24 mmol), thereby obtaining 8.3 g (50% yield) of a final product, [NP(AMPEG1100)$_{0.84}$(IleOEt)$_{1.16}$].

Composition formula: $C_{57}H_{116}N_3O_{26}P$ Elemental analysis: C, 52.21; H, 9.01; N, 4.30 Theoretical value: C, 52.44; H, 8.94; N, 4.10 Hydrogen NMR spectrum (CDCl$_3$, ppm): δ 0.8-1.0 (b, 6H, —NHCH(CH$_2$CH(C$\underline{H}_3$)$_2$COOCH$_2$CH$_3$), δ 1.1-1.3 (b, 3H, —NHCH(CH$_2$CH(CH$_3$)$_2$COOCH$_2$C$\underline{H}_3$), δ 1.4-1.6 (b, 2H, —NHCH(C$\underline{H}_2$CH(CH$_3$)$_2$COOCH$_2$CH$_3$), δ 1.6-1.9 (b, 1H, —NHCH(CH$_2$C$\underline{H}$(CH$_3$)$_2$COOCH$_2$CH$_3$), δ 2.9-3.2 (b, 2H, —NHC$\underline{H}_2$CH$_2$O(CH$_2$CH$_2$O)$_{23}$CH$_3$), δ 3.4 (s, 3H, —NHCH$_2$CH$_2$O(CH$_2$CH$_2$O)$_{23}$C$\underline{H}_3$), δ 3.5-3.9 (b, 95H, —NHCH$_2$C$\underline{H}_2$O(C$\underline{H}_2$C$\underline{H}_2$O)$_{23}$CH$_3$, —NHC$\underline{H}$(CH$_2$CH(CH$_3$)$_2$COOCH$_2$CH$_3$), δ 4.0-4.4 (b, 4H, —NHCH(CH$_2$CH(CH$_3$)$_2$COOC$\underline{H}_2$CH$_3$) Phosphorous NMR spectrum (CDCl$_3$, ppm): δ 18.07 Average molecular weight (M$_w$): 39000

Example 8

Preparation of Poly[poly(aminomethoxyethyleneglycol550)(isolucineethylester)(glycylglycinbenzylester)phosphazene], [NP(AMPEG550)$_{0.72}$ (IleOEt)$_{1.19}$(GlyGlyOBz)$_{0.09}$]

By the same method as described in Example 1, poly (dichlorophosphazene) (2.00 g, 17.26 mmol), triethylamine (4.19 g, 41.42 mmol) and isoleucineethylester hydrogen chloride salt (4.05 g, 20.71 mmol) in the first step, glycylglycinbenzylester hydrogen chloride salt (0.44 g, 1.72 mmol) and triethylamine (0.70 g, 6.88 mmol) in the second step, and poly(aminomethoxyethyleneglycol) (13.29 g, 24.16 mmol) having a molecular weight of 550 and triethylamine (4.89 g, 48.32 mmol) in the third step were respectively used and reacted, thereby obtaining 7.8 g (70% yield) of a final product, [NP(AMPEG550)$_{0.72}$(IleOEt)$_{1.19}$(GlyGlyOBz)$_{0.09}$].

Composition formula: $C_{42}H_{77}N_4O_{16}P$ Elemental analysis: C, 51.01; H, 8.61; N, 6.79 Theoretical value: C, 50.20; H, 8.52; N, 6.68 Hydrogen NMR spectrum (CDCl$_3$, ppm): δ 0.8-1.0 (b, 6H, —NHCH(CH$_2$CH(C$\underline{H}_3$)$_2$COOCH$_2$CH$_3$), δ 1.1-1.3 (b, 3H, —NHCH(CH$_2$CH(CH$_3$)$_2$COOCH$_2$C$\underline{H}_3$), δ 1.4-1.6 (b, 2H, —NHCH(C$\underline{H}_2$CH(CH$_3$)$_2$COOCH$_2$CH$_3$), δ 1.6-1.9 (b, 1H, —NHCH(CH$_2$C$\underline{H}$(CH$_3$)$_2$COOCH$_2$CH$_3$), δ 2.9-3.2 (b, 2H, —NHC$\underline{H}_2$CH$_2$O(CH$_2$CH$_2$O)$_{10}$CH$_3$), δ 3.4 (s, 3H, —NHCH$_2$CH$_2$O(CH$_2$CH$_2$O)$_{10}$C$\underline{H}_3$), δ 3.5-3.9 (b, 95H, —NHCH$_2$C$\underline{H}_2$O(C$\underline{H}_2$C$\underline{H}_2$O)$_{10}$CH$_3$, —NHC$\underline{H}_2$CONHCH$_2$COOCH$_2$C$_6$H$_5$, —NHC$\underline{H}$(CH$_2$CH(CH$_3$)$_2$COOCH$_2$CH$_3$), δ 4.0-4.4 (b, 4H, —NHCH(CH$_2$CH(CH$_3$)$_2$COOC$\underline{H}_2$CH$_3$, —NHCH$_2$CONHC$\underline{H}_2$COOCH$_2$C$_6$H$_5$), δ 5.3-5.4 (b, 2H, —NHCH$_2$CONHCH$_2$COOC$\underline{H}_2$C$_6$H$_5$), δ 7.0-7.3 (b, 5H, —NHCH$_2$CONHCH$_2$COOCH$_2$C$_6$$\underline{H}_5$), Phosphorous NMR spectrum (CDCl$_3$, ppm): δ 17.9 average molecular weight ($M_w$): 47000 maximum gel viscosity ($V_{max}$): 309 Pa·s maximum gel temperature ($T_{max}$): 29° C.

Example 9

Preparation of Poly[poly(aminomethoxyethyleneglycol750)(phenylalanineethylester)phosphazene], [NP(AMPEG750)$_{0.73}$(PheOEt)$_{1.27}$]

By the same method as described in Example 3, poly (dichlorophosphazene) (2.00 g, 17.26 mmol) was reacted with phenylalanineethylester hydrogen chloride salt (5.15 g, 22.44 mmol) in the presence of triethylamine (9.08 g, 89.76 mmol), and then reacted with poly(aminomethoxyethyleneglycol) (18.12 g, 24.16 mmol) of a molecular weight of 750 in the presence of triethylamine (4.89 g, 48.33 mmol) thereby obtaining 9.4 g (yield 65%) of a final product, [NP(AMPEG750)$_{0.73}$(PheOEt)$_{1.27}$].

Composition formula: $C_{44}H_{82}N_3O_{18}P$ Elemental analysis: C, 55.00; H, 8.24; N, 5.31 Theoretical value: C, 54.74; H, 8.14; N, 5.03 Hydrogen NMR spectrum (CDCl$_3$, ppm): δ 0.8-1.05 (b, 3H, —NHCH(CH$_2$C$_6$H$_5$)COOCH$_2$C$\underline{H}_3$), δ 2.9-3.2 (b, 4H, —NHCH(C$\underline{H}_2$C$_6$H$_5$)COOCH$_2$CH$_3$), —NHC$\underline{H}_2$CH$_2$O(CH$_2$CH$_2$O)$_{15}$CH$_3$), δ 3.4 (s, 3H, —NHCH$_2$CH$_2$O(CH$_2$CH$_2$O)$_{15}$C$\underline{H}_3$), δ 3.5-3.9 (b, 95H, —NHCH2C$\underline{H}_2$O(C$\underline{H}_2$C$\underline{H}_2$O)$_{15}$CH$_3$, —NHC$\underline{H}$(CH$_2$C$_6$H$_5$)COOCH$_2$CH$_3$), δ 4.0-4.4 (b, 2H, —NHCH(CH$_2$C$_6$H$_5$)COOC$\underline{H}_2$CH$_3$), δ 7.0-7.3 (b, 5H, —NHCH(CH$_2$C$_6$$\underline{H}_5$)COOCH$_2$CH$_3$), Phosphorous NMR spectrum (CDCl$_3$, ppm): δ 17.6 Average molecular weight ($M_w$): 255000

Example 10

Preparation of Poly[poly(aminomethoxyethyleneglycol550)(leucineethylester)phosphazene], [NP(AMPEG550)$_{0.69}$(LeuOEt)$_{1.31}$]

By the same method as described in Example 3, poly (dichlorophosphazene) (2.00 g, 17.26 mmol) was reacted with leucineethylester hydrogen chloride salt (4.56 g, 23.30 mmol) in the presence of triethylamine (9.43 g, 93.20 mmol), and then reacted with poly(aminomethoxyethyleneglycol)(12.34 g, 22.44 mmol) of a molecular weight of 550 in the presence of triethylamine (4.54 g, 44.88 mmol), thereby obtaining 8.2 g (yield 75%) of a final product, [NP(AMPEG550)$_{0.69}$(LeuOEt)$_{1.31}$].

Composition formula: $C_{31}H_{64}N_3O_{13}P$ Elemental analysis: C, 50.45; H, 8.79; N, 6.91 Theoretical value: C, 50.21; H, 8.65; N, 6.67 Hydrogen NMR spectrum(CDCl$_3$, ppm): δ 0.8-1.0 (s, 6H, —NHCH(CH$_2$CH(C$\underline{H}_3$)$_2$)COOCH$_2$CH$_3$), δ 1.1-1.3 (s, 6H, —NHCH(CH$_2$CH(CH$_3$)$_2$)COOCH$_2$C$\underline{H}_3$), δ 1.4-1.6 (b, 2H, —NHCH(C$\underline{H}_2$CH(CH$_3$)$_2$)COOCH$_2$CH$_3$), δ 1.6-1.9 (b, 1H, —NHCH(CH$_2$C$\underline{H}$(CH$_3$)$_2$)COOCH$_2$CH$_3$), δ 2.9-3.2 (b, 2H, —NHC$\underline{H}_2$CH$_2$O(CH$_2$CH$_2$O)$_{10}$CH$_3$), δ 3.4 (s, 3H, —NHCH$_2$CH$_2$O(CH$_2$CH$_2$O)$_{10}$C$\underline{H}_3$), δ 3.5-3.9 (b, 29H, —NHCH$_2$C$\underline{H}_2$O(C$\underline{H}_2$C$\underline{H}_2$O)$_{10}$CH$_3$, —NHCH(CH$_2$CH(CH$_3$)$_2$)COOCH$_2$CH$_3$), δ 4.0-4.4 (b, 4H, —NHCH(CH$_2$CH(CH$_3$)$_2$)COOC$\underline{H}_2$CH$_3$), Phosphorous NMR spectrum(CDCl$_3$, ppm): δ 17.9 Average molecular weight ($M_w$): 143000 Maximum gel viscosity ($V_{max}$): 6.2 Pa·s Maximum gel temperature ($T_{max}$): 44° C.

Example 11

Observation of Sol-Gel Change of Polyphosphazene

The polyphosphazene polymer according to the examples of the present invention and the polyphosphazene polymer as disclosed in *Macromolecules* 35, 3876 (2002) were respectively dissolved in pH 7.4 PBS solution in a concentration of 10 weight % each, and a sol-gel behavior with a temperature change was observed.

Figure 1:
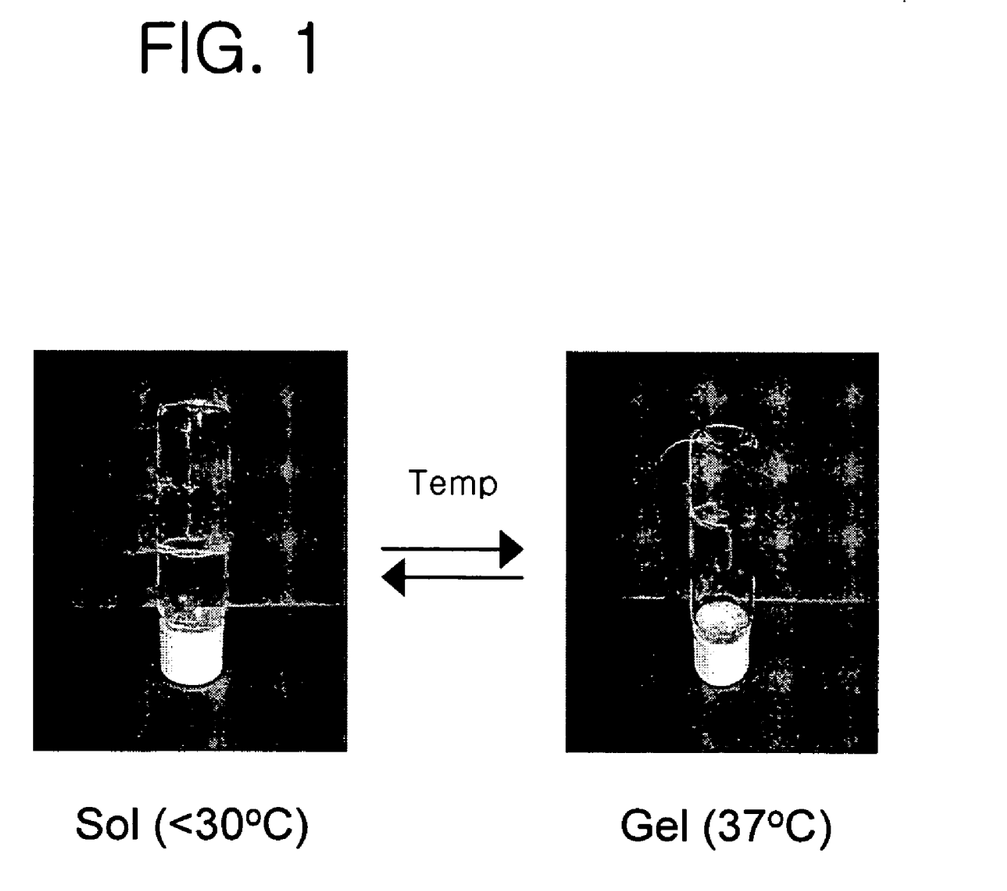
FIG. 1 is a picture showing a sol-gel behavior of a polyphosphazene according to Example 4 of the present invention.

FIG. 1 is a picture showing a sol-gel behavior of the polyphosphazene polymer according to the present invention with a temperature change. As shown in FIG. 1, the polymer is a solution state at a temperature lower than 30° C. but it is changed into a gel state at a temperature near a body temperature (37° C.).

The following Table 1 shows the results of the experiment of gel characteristic of the polyphosphazene polymer (polymer 1 and 2) disclosed in *Macromolecules* 35, 3876 (2002) and the polyphosphazene polymer prepared in Examples 1 to 4 of the present invention according to a temperature change.

TABLE 1

| Polymer | structure | Starting gel temperature (° C.) | Maximum gel temperature (° C.) | Maximum gel intensity (Pa · S) | $M_w$ (×10$^{-4}$)[e] |
|---|---|---|---|---|---|
| 1 | [NP(IleuOEt)$_{0.94}$(AMPEG350)$_{1.06}$]$_n$ | 5 | 29 | 37.2 | 3.9 |
| 2 | [NP(IleuOEt)$_{1.24}$(AMPEG550)$_{0.76}$]$_n$ | 26 | 52 | 6.7 | 2.1 |

TABLE 1-continued

| Polymer structure | Starting gel temperature (° C.) | Maximum gel temperature (° C.) | Maximum gel intensity (Pa · S) | $M_w$ $(\times 10^{-4})^e$ |
|---|---|---|---|---|
| Example 1 [NP(IleuOEt)$_{1.18}$(AMPEG550)$_{0.78}$(GlyLacOEt)$_{0.04}$]$_n$ | 25 | 43 | 312.8 | 2.7 |
| Example 2 [NP(IleuOEt)$_{1.20}$(AMPEG550)$_{0.70}$(GlyGlyOEt)$_{0.10}$]$_n$ | 21 | 39 | 550.0 | 4.1 |
| Example 3 [NP(IleuOEt)$_{1.20}$(AMPEG550)$_{0.80}$]$_n$ | 27 | 40 | 400.0 | 4.2 |
| Example 4 [NP(IleuOEt)$_{1.35}$(AMPEG750)$_{0.65}$]$_n$ | 13 | 47 | 680.0 | 2.2 |

In table 1, "Starting gel temperature" denotes a temperature at the time when the viscosity of an aqueous solution of a polymer (10 weight % PBS solution, pH 7.4) starts to be remarkably increased, "maximum gel temperature" denotes a temperature that a viscosity of an aqueous solution of a polymer (10 weight % PBS solution, pH 7.4) reaches to a maximum point, and "maximum gel intensity" denotes a viscosity that a viscosity of an aqueous solution of a polymer (10 weight % PBS solution, pH 7.4) reaches to a maximum point.

Figure 2:
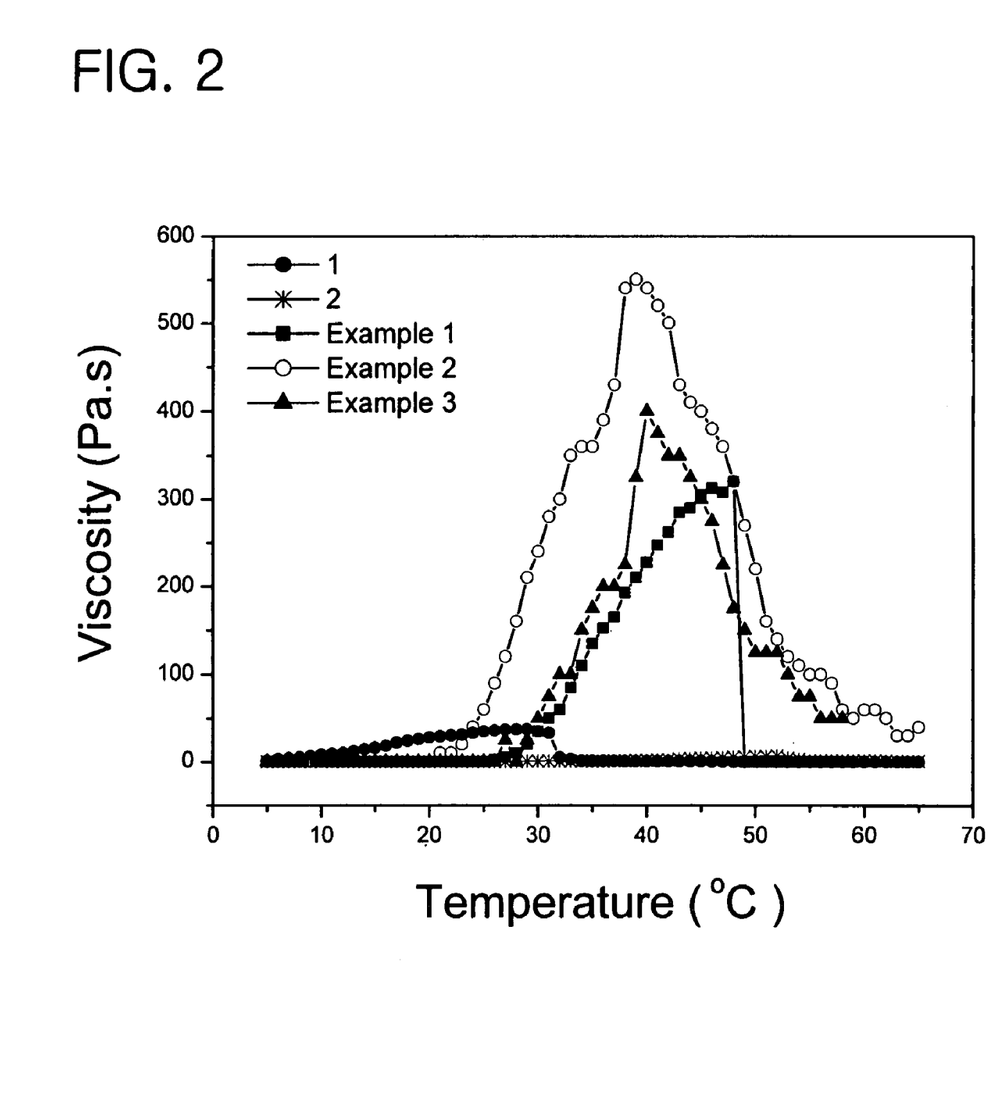
FIG. 2 shows a viscosity change of a polymer (10 weight % PBS solution, pH 7.4) according to a temperature change.
Figure 3:
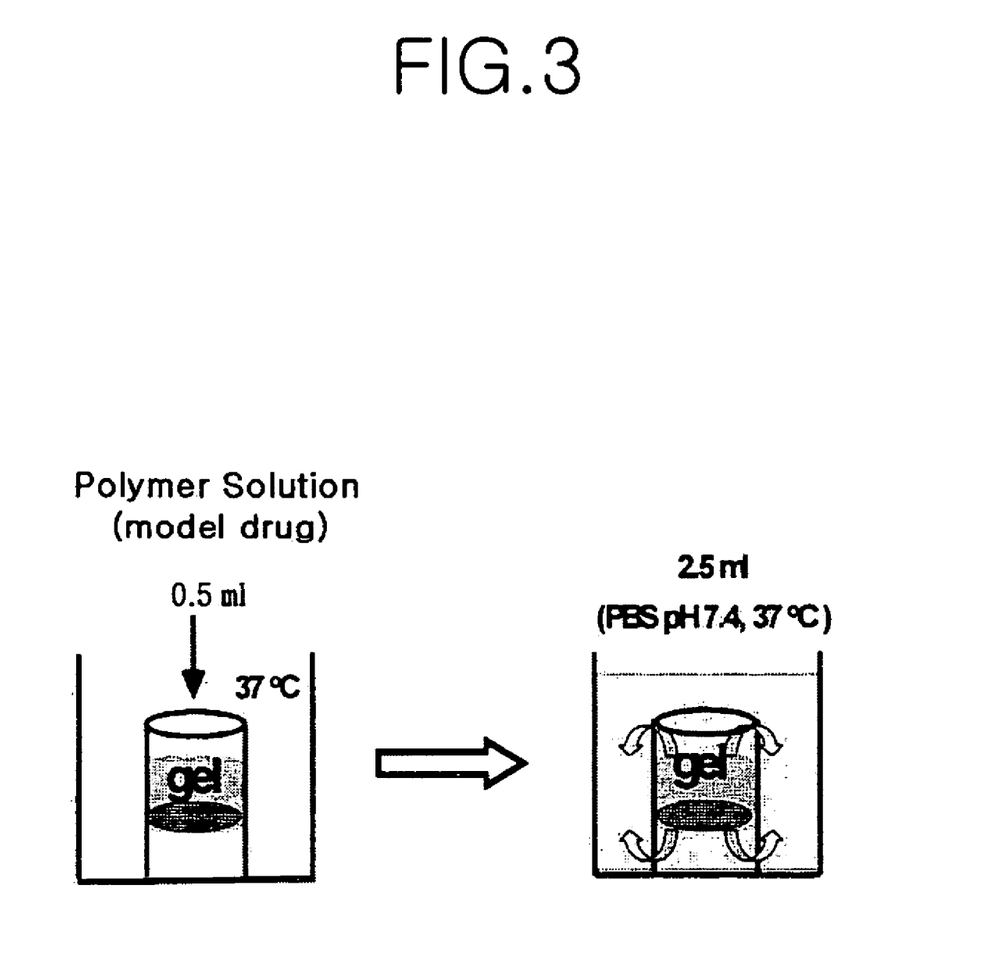
FIG. 3 shows a model of a release experiment of a model drug (FITC-Dextran) of polyphosphazene hydrogels.

FIG. 2 shows a viscosity change of the polyphosphazene polymer represented as the polymers 1 and 2 in the table 1 and the polyphosphazene polymer according to Examples 1 to 3 of the present invention, due to a temperature change.

As shown in Table 1 and FIG. 2, in case of the Polymer 1, the maximum gel temperature was 29° C. and the gel was contracted before the temperature reached to 37° C.; in case of the Polymer 2, although the maximum gel temperature was 52° C. but the gel intensity was very weak. Therefore, it can be seen that the polymers 1 and 2 are not suitable for being used as a drug delivering material.

Contrary to this, the polyphosphazene polymer prepared in Examples 1 to 4 of the present invention not only maintains the transparent gel characteristic at a temperature near 37° C., but also has a gel intensity enough to be used as a drug delivering material.

Example 12

Drug Release Behavior Experiments of Polyphosphazene Gel Polymer

Drug release behavior experiments of the polyphosphazene polymer represented as the polymer 1 in Table 1 and the polyphosphazene polymers according to Examples 2 to 4 of the present invention were performed as follows.

FITC-dextran (FITC-dextran, Mw 71,600) was used as a model drug for in vitro release behavior experiments of the polyphosphazene polymer. First, an experiment object polymer was dissolved in a concentration of 10 weight % PBS solution, pH 7.4 at 4° C. Next, the model drug was put in a concentration of 0.1 weight % and then stirred at a low temperature to obtain a uniform solution. As soon as 0.5 ml of said solution was put into a container maintained as 37° C., it became a gel state at once. To the resulting material, 2.5 ml of pH 7.4 PBS solution was added and the drug release experiments were carried out.

Samples were taken from the solution at a certain time interval thus to measure a fluorescence intensity, thereby calculating an amount of released drug.

Figure 4:
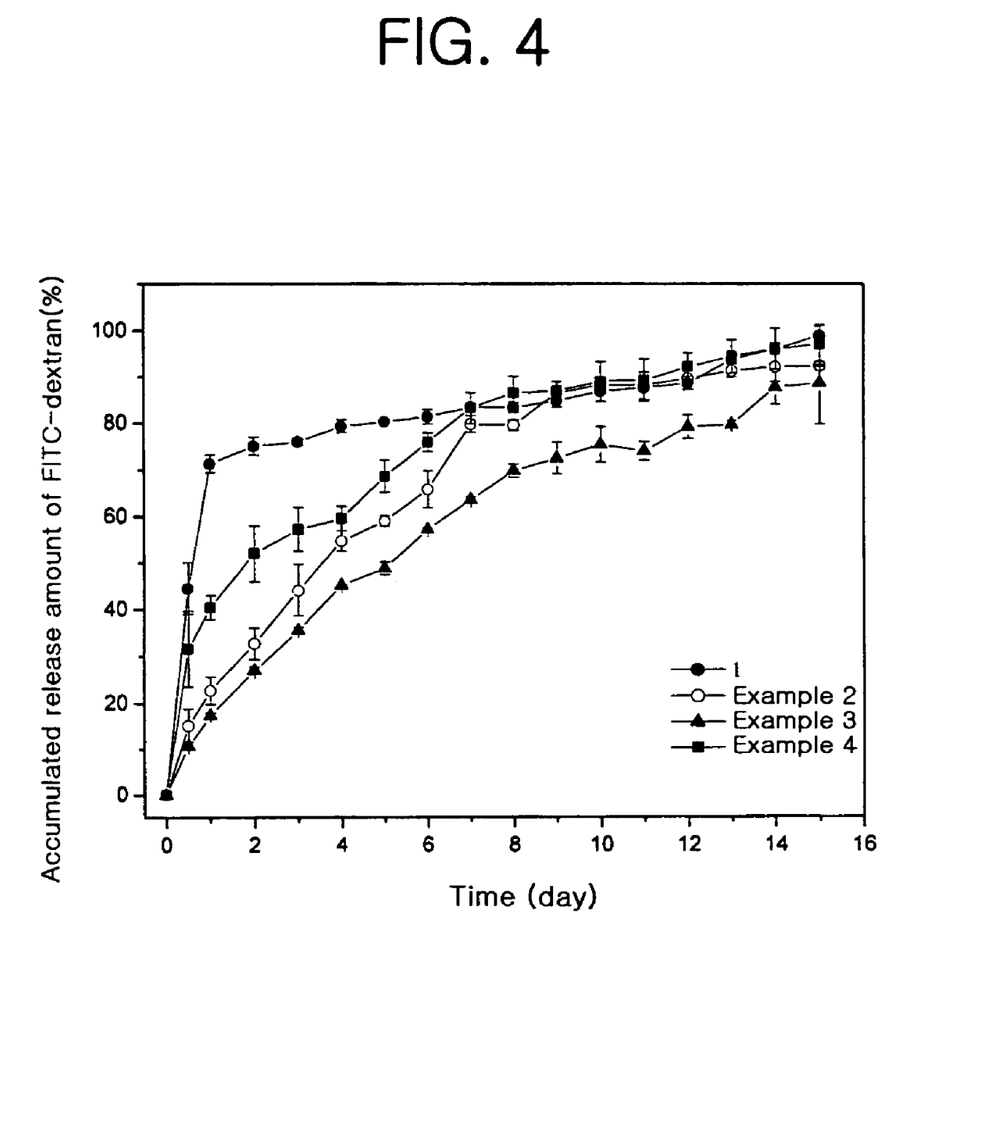
FIG. 4 shows an experiment result of a release experiment of a model drug (FITC-Dextran) of polyphosphazene hydrogels.

The result was shown in FIG. 4, from which it is noted that drug was gradually released for more than 15 days in most gels.

However, in case of the polymer 1, drug more than 70% which corresponds to much greater quantity than that of the polymers of the present invention was released on the first day. The reason why an initial release amount of the drug was great is because the gel made of the polymer 1 was contracted in pH 7.4 PBS aqueous solution of 37° C.

Contrary to this, in case of the polymers prepared in the Examples 2 to 4 of the present invention, an initial drug release amount was less (within 40%) and drug was gradually released for more than 15 days. The reason is because the gel was not contracted even at 37° C. and the gel intensity was maintained.

In the meantime, it was shown that the polymers of Examples 2 and 3 have less initial drug release amount than the polymer of Example 4. The reason is because the polymers of Examples 2 and 3 have the maximum gel temperature near 37° C. but the polymer of Example 4 has the maximum gel temperature of 47° C. That is, the polymer of Example 4 has a greater hydrophilic property than the polymers of Examples 2 and 3 thus to be dissolved in water better, and thereby drug is released faster.

In the present invention, the polyphosphazene polymer having a thermosensitive hydrogel characteristic that a sol state maintained in a low temperature is changed into a gel state near a body temperature and suitable for being used as an injectable drug delivering material, the preparation method thereof, and the injectable thermosensitive hydrogels using the same were provided.

The polyphosphazene polymer according to the present invention not only has a thermosensitive characteristic and a biodegradable characteristic in aqueous water, but also has proper characteristics for being used as an injectable drug delivering material such as a gelation temperature, a gel intensity, a decomposition speed, a drug release behavior, and etc.

Therefore, the polymer according to the present invention is useful as an injectable material for delivering drugs and can be applied to various industry fields relevant to a tissue engineering.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A polyphosphazene polymer represented by formula 1:

Formula 1 wherein,

R represents $CH_2CH(CH_3)_2$, $CH(CH_3)C_2H_5$ or $C_7H_7$, R' denotes $CH_2COOC_2H_5$ or $CH(CH_3)COOC_2H_5$, and R" denotes $OC_2H_5$, $NHCH_2COOC_2H_5$, $NHCH_2COOC_7H_7$, $NHCH(CH_2CH(CH_3)_2)COOC_2H_5$ or $NHCH(CH(CH_3)C_2H_5)COOC_2H_5$;

a and b are independently 0.1-1.9, c and d are independently 0-1.9, and a+b+c+d=2.0;

n is an integer of 10-10000; and m is an integer of 10-50; and wherein if the molecular weight of $HN-(CH_2-CH_2-O-)_m-CH_3$ is 550, then c is not 0.

2. A method for preparing the polyphosphazene polymer of Formula 1, comprising the steps of:

(1) reacting a polydichlorophosphazene of Formula 3 with amino acid ethylester of Formula 4 in a mol ratio of 1:0.1-1.9;

(2) reacting the product of the step (1) with 0-1.9 equivalents of the compound of Formulas 5 or 6; and (3) reacting the product of the step (2) with two equivalents of aminomethoxypolyethyleneglycol of Formula 7, based on the remaining chlorine groups Formula 1

Formula 3

$H_2NCH(R)COOCH_2CH_3$  Formula 4

$H_2NCH_2COOR'$  Formula 5

$H_2NCH_2COR''$  Formula 6

[Formula 7]

wherein,

R represents $CH_2CH(CH_3)_2$, $CH(CH_3)C_2H_5$ or $C_7H_7$, R' denotes $CH_2COOC_2H_5$ or $CH(CH_3)COOC_2H_5$, and R" denotes $OC_2H_5$, $NHCH_2COOC_2H_5$, $NHCH_2COOC_7H_7$, $NHCH(CH_2CH(CH_3)_2)COOC_2H_5$ or $NHCH(CH(CH_3)C_2H_5)COOC_2H_5$;

a and b are independently 0.1-1.9, c and d are independently 0-1.9, and a+b+c+d=2.0;

n is an integer of 10-10000; and m is an integer of 10-50; and wherein if molecular weight of the compound of Formula 7 is 550, then c is not 0.

3. The method of claim 2, wherein the reaction mixtures of each step is used in the next step without purification.

4. The method of claim 2 or 3, wherein a solvent selected from the group consisting of tetrahydrofuran, dioxane, dimethylformamide, chloroform, and toluene is used in the steps (1) and (3), and acetonitrile is used as a reaction solvent in the step (2).

5. The method of claim 2 or 3, wherein the said aminomethoxypolyethyleneglycol has a molecular weight of 550-2500.

6. The method of claim 2 or 3, further comprising a step of forming precipitates by adding ethyl ether or hexane to the reaction mixture after the step (3) is completed, then dissolving the solid obtained by filtering the mixture in methanol, and dialyzing with methanol and distilled water for 3-10 days each, then drying at a low temperature, thereby recovering the pure compound of Formula 1.

7. The method of claim 2, wherein the amino acid ethylester compound of Formula 4 is used in the form of a hydrogen chloride salt.

8. The method of claim 2, wherein the compound of Formula 6 or 7 is used as oxalate or hydrogen chloride salt thereof.

9. The method of claim 7 or 8, wherein the reaction is carried out in the presence of triethylamine.

10. Injectable thermosensitive hydrogels for delivering drug having a sol-gel characteristic with a temperature change, wherein the hydrogels are the polyphosphazene polymer of claim 1 dissolved in buffering solution, acid solution, base solution, salt solution or water in a concentration of 2-30 weight %.

* * * * *